United States Patent
Louret et al.

(10) Patent No.: US 9,593,355 B2
(45) Date of Patent: Mar. 14, 2017

(54) PROCESS FOR THE PRODUCTION OF OPTIMISED LIQUEFIED LIGNOCELLULOSIC SUBSTRATE

(71) Applicant: IFP ENERGIES NOUVELLES, Rueil-Malmaison Cedex (FR)

(72) Inventors: Sylvain Louret, Lyons (FR); Romain Rousset, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 61 days.

(21) Appl. No.: 14/364,081

(22) PCT Filed: Nov. 29, 2012

(86) PCT No.: PCT/FR2012/000493
§ 371 (c)(1),
(2) Date: Jun. 10, 2014

(87) PCT Pub. No.: WO2013/088001
PCT Pub. Date: Jun. 20, 2013

(65) Prior Publication Data
US 2014/0377812 A1 Dec. 25, 2014

(30) Foreign Application Priority Data
Dec. 14, 2011 (FR) ...................... 11 03856

(51) Int. Cl.
C12P 19/14 (2006.01)
C12P 7/10 (2006.01)
C12P 19/02 (2006.01)
C13K 1/02 (2006.01)

(52) U.S. Cl.
CPC ............... *C12P 19/14* (2013.01); *C12P 7/10* (2013.01); *C12P 19/02* (2013.01); *C13K 1/02* (2013.01); *Y02E 50/16* (2013.01)

(58) Field of Classification Search
None
See application file for complete search history.

(56) References Cited

U.S. PATENT DOCUMENTS

| 3,642,580 A * | 2/1972 | Ghose ............................ 435/105 |
| 4,409,329 A | 10/1983 | Silver |
| 7,807,419 B2 | 10/2010 | Hennessey et al. |
| 2009/0053777 A1 | 2/2009 | Hennessey et al. |
| 2010/0297705 A1 * | 11/2010 | Medoff ............... C12M 45/02 435/72 |
| 2011/0177558 A1 * | 7/2011 | Medoff et al. ................ 435/72 |
| 2013/0217074 A1 | 8/2013 | Sjoede et al. |
| 2014/0004571 A1 | 1/2014 | Garrett et al. |

FOREIGN PATENT DOCUMENTS

| WO | 2011157427 A1 | 12/2011 |
| WO | 2013082616 A2 | 6/2013 |

OTHER PUBLICATIONS

ATSM (ATSM E1756-01, Standard Test Method for Determination of Total Solids in Biomass, available at http://compass.astm.org/EDIT/html_historical.cgi?E1756+01).*
International Search Report from PCT/FR2012/000493 dated Sep. 30, 2013.
Kyle W. Dunaway et al. "Characterization of changes in viscosity and insoluble solids content during enzymatic saccharification of pretreated corn stover slurries" Bioresource Technology, [2010], vol. 101, pp. 3575-3582.
David B. Hodge et al. "Model-Based Fed-Batch for High-Solids Enzymatic Cellulose Hydrolysis" Applied Biochemistry and Biotechnology, [2009], vol. 152, No. 1, pp. 88-107. (published online: May 30, 2008).
Byung-Hwan Um et al. "A Comparison of Simple Rheological Parameters and Simulation Data for Zymomonas mobilis Fermentation Broths with High Substrate Loading in a 3-L Bioreactor" Applied Biochemistry and Biotechnology, [2008], vol. 145, No. 1-3, pp. 29-38.
M.R. Ehrhardt et al. "Rheology of Dilute Acid Hydrolyzed Corn Stover at High Solids Concentration" Applied Biochemistry and Biotechnology, [2010], vol. 160, No. 4, pp. 1102-1115. (published online: Mar. 31, 2009).

(Continued)

Primary Examiner — Robert Yamasaki
Assistant Examiner — Charles Zoltan Constantine
(74) Attorney, Agent, or Firm — Millen, White, Zelano, Branigan, P.C.

(57) ABSTRACT

The present invention concerns a production of liquefied lignocellulosic substrate by enzymatic reaction. 10% to 40% by weight dry matter of pre-treated lignocellulosic substrate is contacted, with water and enzymes at 0.1 to 60 mg of enzymes per gram of cellulose for a period of 1 to 24 hours. Over time, at least the value of one of the rheological characteristics of the reaction medium is measured. If a reduction of the value is detected over time, the following step a) is carried out:
 a) the feeding flow rate of pre-treated lignocellulosic substrate is increased, with or without modification of the flow rate of enzymes and/or water;
If an increase of the value is detected over time, a step b) is carried out:
 b) the feeding flow rate of water and/or enzymes is increased, with or without modification of the flow rate of pre-treated lignocellulosic substrate.

24 Claims, No Drawings

(56) References Cited

OTHER PUBLICATIONS

Nora Szijarto et al. "Thermostable endoglucanases in the liquefaction of hydrothermally pretreated wheat straw" Biotechnology for Biofuels, [2011], vol. 4, pp. 1-10.

S.P. Shoemaker et al. "Enzymic Activities of Endo-1,4-β-D-Glucanases Purified from Trichoderma Viride" BBA Enzymology, [1978], vol. 523, No. 1, pp. 133-146.

Claudia C. Geddes et al. "Optimizing cellulase usage for usage for improved mixing and rheological properties of acid-pretreated sugarcane bagasse" Bioresource Technology, [2010], vol. 101, pp. 9128-9136.

\* cited by examiner

PROCESS FOR THE PRODUCTION OF OPTIMISED LIQUEFIED LIGNOCELLULOSIC SUBSTRATE

FIELD OF THE INVENTION

The present invention relates to a process for the production of liquefied lignocellulosic substrate from lignocellulosic biomass. Said liquefied lignocellulosic substrate may then be used in various subsequent steps such as, for example, in a fermentation step for the production of alcohols, or for the production of intermediates for chemistry.

PRIOR ART

The development of economically viable processes for upgrading lignocellulosic biomass is currently a "hot topic". The increasing scarcity of fossil resources and competition with food supplies have resulted in a search for novel pathways to the production of biofuels and chemical intermediates.

Since the 1970s, the transformation of lignocellulosic biomass after hydrolysis of the constituent polysaccharides into sugars has been the subject of many studies.

Lignocellulosic biomass is characterized by a complex structure constituted by three principal polymers, cellulose, hemicelluloses and lignin, the proportions of which vary as a function of the species of lignocellulosic biomass. A typical but not limiting composition is as follows: the cellulose is in a quantity in the range 35% to 50%, the hemicelluloses, which are polysaccharides essentially constituted by pentoses and hexoses, are in a quantity in the range 20% to 30% and the lignins are in a quantity in the range 15% to 25% by weight. Degradation of the biomass proves to be difficult, since the polysaccharides of the plant wall (cellulose and hemicelluloses) are intimately associated with lignin, which provides the walls with rigidity.

Of these three polymers, cellulose is the principal source of sugars, as it is constituted by glucose; this latter is readily upgraded.

Conventionally, processes for upgrading biomass by a biochemical pathway comprise a plurality of steps. A first step is collection and transport of the lignocellulosic biomass to a biomass transformation centre. The second step is the pre-treatment or pre-hydrolysis of the biomass, which renders the cellulose accessible to the enzymes and thus capable of producing a pre-treated lignocellulosic substrate. The third step, enzymatic hydrolysis, means that, because a solution of cellulolytic and hemicellulolytic enzymes produced by microorganisms and known as an enzymatic cocktail is used, cellulose is transformed into glucose. This glucose may then be upgraded, for example to ethanol, during a fourth step of fermentation, generally by the yeast *Saccharomyces cerevisiae*, or to an acetone, butane, ethanol (ABE) mixture by fermentation with the yeast *Clostridium acetobutylicum*. A fifth step, distillation, then means that the molecules obtained can be concentrated.

Said pre-treated lignocellulosic substrate obtained at the end of the pre-treatment step is a solid residue essentially composed of cellulose and solid lignin.

Throughout the remainder of the text, the concentration of pre-treated lignocellulosic substrate is expressed as the percentage by weight of dry matter. The dry matter content, expressed as the percentage by weight, is the ratio of the mass of the sample obtained after drying at 105° C. for 24 hours over the initial mass of the sample.

In the enzymatic hydrolysis step, said pre-treated lignocellulosic substrate has to be mixed with a liquid solution containing cellulolytic and hemicellulolytic enzymes. The aim is to obtain a high concentration of sugars, and so the enzymatic hydrolysis step has to be carried out at high concentrations of pre-treated lignocellulosic substrate, i.e. a high dry matter content. Intimate mixing with said liquid solution containing the cellulolytic and hemicellulolytic enzymes thus proves to be difficult.

Thus, the enzymatic hydrolysis step can be carried out with a pre-treated lignocellulosic substrate diluted by adding water in order to homogenize the reaction medium. Diluting said lignocellulosic substrate with water has the disadvantage of also diluting the sugars and oligomers of sugars obtained at the end of the enzymatic hydrolysis step. In order to overcome this dilution problem and to be able to have an advantageous and viable concentration of sugar, specific implementations may be envisaged: feeding said lignocellulosic substrate in "fed batch" mode, defined below, means that a reactor starter liquor can be prepared which is sufficiently dilute to be able to initiate the enzymatic hydrolysis reaction and provide for good mixing. As the reaction progresses, the mixture becomes more and more liquid, and it is possible to add fresh substrate in order to increase its concentration. By operating in this manner, it is then possible to obtain high concentrations of substrate which are advantageously in the range 20% to 30% by weight dry matter.

This commencement of hydrolysis with a high dry matter content poses problems with mixing and homogenization. The reaction medium is very pasty and viscous, which demands specific agitation which is much more complex than that necessary at the end of hydrolysis where the reaction mixture has become more liquid. For this reason, it appears to be pertinent to separate this hydrolysis into two steps:
  liquefaction, corresponding to the start of hydrolysis, during which the reaction medium is viscous and demands a complex agitation system and a high agitation energy. In contrast, the residence time is short, which means that the volumes to be provided with such agitation are limited;
  the next step corresponds to saccharification in the case in which hydrolysis is continued in a conventional manner, or to SSF (simultaneous saccharification and fermentation) in the case in which yeasts are introduced to ferment the sugars while carrying out the hydrolysis. This step demands simpler agitation, less energy, but a longer residence time and thus a large volume.

The Applicant's research has more particularly been focussed on the liquefaction step in order to monitor its progress and optimize control thereof.

Thus, the present invention proposes to monitor the measurement of a rheological characteristic of the reaction medium so as to optimize the liquefaction, while adjusting the additions of lignocellulosic substrate, enzyme or the dilution.

One aim of the process of the present invention is thus to provide a process for the production of liquefied lignocellulosic substrate, by enzymatic reaction in order to obtain a liquefied lignocellulosic substrate with a rheology which is compatible with its transfer to the step located downstream and also with its agitation in the next reaction.

Patent application US 2010/0255554 describes a process for the hydrolysis of lignocellulosic biomass in "fed batch" mode, in which the functional parameters of the process are adjusted by controlling the volume of the reactor and/or the frequency of addition of the pre-treated lignocellulosic biomass feed and optionally the addition of enzymes, and the volume and/or concentration of sugars produced in the reactor. In particular, the pre-treated lignocellulosic biomass feed is added to the reactor in a sequential manner, each time such that 70% to 90% theoretical conversion of the cellulose to glucose is obtained in the reaction medium. Thus, monitoring the measurement of the concentration of the sugars produced constitutes the optimization criterion of the process. Thus, this method requires knowledge of the theoretical conversion rate for a given substrate which, because of the variability of potentially treated substrates, is difficult to apply.

Hodge et al., Model-Based Fed-Batch for High-Solids Enzymatic Cellulose Hydrolysis, Appl. Biochem Biotechnol. (2009) 152:88-107, describes a process for the hydrolysis of lignocellulosic biomass in "fed batch" mode based on modelling the hydrolysis reaction. Thus, for each substrate or mixture of substrates, it is necessary to determine their behaviour during hydrolysis in order to determine the best strategy for adding feed to the reactor.

Rosgaard et al., Effects of Substrate Loading on Enzymatic Hydrolysis and Viscosity of Pretreated Barley Straw, Appl. Biochem Biotechnol. (2007) 143:27-40, examines the effect of various strategies for the addition of pre-treated lignocellulosic substrate on the yields of sugars from enzymatic hydrolysis. It describes the well-known phenomenon of a drop in viscosity as the reaction advances. The disclosure of that article is such that it is not possible to generalize the substrate supply strategy and/or the enzymatic solution in the event of a change of substrate and does not take into account the mechanical constraints of agitation.

Patent application US2010/330638A describes a "fed batch" mode feed for the enzymatic hydrolysis step, indicating therein that tests can determine the quantity of biomass which can be added to each batch. Thus, it is necessary to carry out tests prior to the enzymatic hydrolysis test every time the substrate type is changed.

In contrast to the prior art, the present invention proposes a process for the production of liquefied lignocellulosic substrate in which the measurement of a rheological characteristic of the reaction medium is monitored in order to optimize liquefaction.

In particular, the present invention proposes a process for the production of liquefied lignocellulosic substrate by enzymatic reaction, in which 10% to 40% by weight dry matter of pre-treated lignocellulosic substrate is brought into contact, with agitation, with water and with enzymes at a concentration in the range 0.1 to 60 mg of enzymes per gram of cellulose for a period in the range 1 to 24 hours, said process being characterized in that over time, at least the value of one of the rheological characteristics of the reaction medium is measured and in that if a reduction in said value is detected over time, the following step a) is carried out:
  a) the feeding flow rate of pre-treated lignocellulosic substrate is increased, with or without modification of the flow rate of enzymes and/or water; and in that if an increase in said value is detected over time, a step b) is carried out as follows:
  b) the feeding flow rate of water and/or enzymes is increased, with or without modification of the flow rate of pre-treated lignocellulosic substrate.

One advantage of the present invention is the provision of a process for the production of liquefied lignocellulosic substrate which can be carried out in an automated manner, independently of the treated substrate.

Another advantage of the present invention is the provision of a process for the production of liquefied lignocellulosic substrate which does not require prior characterization of the treated substrate, thereby providing for greater flexibility in the plant and increased ease of use.

In addition, the present invention does not require the development of a reaction model and thus remains pertinent irrespective of the type of substrate or enzymatic cocktail employed.

Another advantage of the present invention is the provision of a process for the production of liquefied lignocellulosic substrate which can be used to monitor and provide for easy adaptation to a change in the reaction medium which does not necessitate complex measures, such as the concentration of sugars in the medium, for example.

DETAILED DESCRIPTION OF THE INVENTION

The pre-treated lignocellulosic substrate used in the process of the present invention is advantageously obtained using conventional processes for the pre-treatment of lignocellulosic biomass such as acid cooking, alkaline cooking, steam explosion, organosolv, etc., for example. Acid type pre-treatments under mild conditions and by steam explosion are the most suitable. They provide the cellulose with good accessibility to hydrolysis.

The process of the present invention is advantageously a liquefaction process. Said process is advantageously carried out in a reactor with a cylindrical shape with a height/diameter ratio which is advantageously in the range 1 to 3.

Said reactor can be used to treat viscous media having a variable viscosity and thus to use lignocellulosic substrate dry matter contents which may reach 40% by weight. The high dry matter contents and the high viscosity of the reaction medium requires that the reactor should be equipped with an agitator allowing for good contact between enzyme and substrate and good homogeneity. Conventionally, the agitator which is selected must be able to treat laminar flows. Broad agitators, or even those scraping the wall of the reactor with moderate rotation rates and exerting a mixing and kneading action are preferred. One example of a particularly suitable agitator is the Paravisc (EKATO) which can also be used with an added baffle which breaks the motion of the assembly.

In accordance with the invention, in the process of the present invention, the pre-treated lignocellulosic substrate is brought into contact at a concentration in the range 10% to 40% by weight of dry matter of pre-treated lignocellulosic substrate, preferably at a concentration in the range 16% to 30% by weight of dry matter and preferably in the range 18% to 24% by weight of dry matter.

In accordance with the invention, the enzymes are brought into contact in the process of the present invention at a concentration in the range 0.1 to 60 mg of enzymes per gram of cellulose, preferably at a concentration in the range 5 to 30 mg of enzymes per gram of cellulose and more preferably in the range 10 to 20 mg of enzymes per gram of cellulose.

In accordance with the invention, the contact period is in the range 1 to 24 hours, preferably in the range 2 to 12 hours and more preferably in the range 4 to 8 hours.

Said process of the present invention is characterized in that a measurement over time of at least the value of one of the rheological characteristics of the reaction medium is carried out.

Said rheological characteristics of the reaction medium are advantageously selected from the viscosity of the reaction medium, the torque of the shaft of the agitation system and the electrical power consumed by the motor. The electrical power consumed by the motor is denoted $P_{elec}$.

During the process of the invention, i.e. during liquefaction, the viscosity of the reaction medium, the torque on the shaft of the agitation system and the electrical power consumed by the motor are rheological characteristics of the lignocellulosic substrate produced to be monitored which have a number of advantages. In fact, said characteristics: viscosity, torque and power, are interrelated. The electrical power consumed by the motor, $P_{elec}$, is related to the mechanical power $P_{mec}$ driving the agitator shaft.

The electrical power consumed by the motor is a parameter which is conventionally measured and monitored on pilot or industrial plants.

The following formulae define the relationships between the various parameters:

$P_{mec} = f(P_{elec})$, f being a design feature of the motor and being given by the manufacturer of the motor;

$P_{mec} = 2\pi N \cdot C$, in which:

N is the agitation rate in rotations per second;

C is the torque in N·m, and $P_{mec}$ is the power in watts.

During agitation, the following relationship holds:

$P_{mec} = \rho N_p N^3 D^5$

ρ is the density of the reaction medium in kg·m$^{-3}$;

D is the external diameter of the agitator in m;

$N_p$ is a characteristic of the agitator which is dependent on the geometry of the vessel and the flow conditions.

Under laminar flow conditions, the following relationship holds:

$N_p = A/Re$, from which $P_{mec} = \rho A N^3 D^5 / Re$ where A is a constant of the agitation system, Re is the Reynolds number and $Re = \rho N D^2 / \bar{\mu}$, $\bar{\mu}$ being the mean dynamic viscosity, measured in Pascal second (Pa·s), of the reaction medium, with $\bar{\mu} = P_{mec}/(AN^2D^3) = 2\pi C/(AD^3N)$.

If the viscosity and the torque of the agitation system shaft are measurements which are readily accessible on a small scale, the electrical power consumed by the motor, $P_{elec}$, is the parameter which is most easily measured on an industrial scale.

Highly preferably, said process of the present invention is characterized in that a measurement of the electrical power consumed by the motor over time is carried out.

The change in the electrical power consumed by the motor is thus correlated to the liquefaction of the pre-treated lignocellulosic substrate and to the progress of the reaction.

If the power drops, this means that the pre-treated lignocellulosic substrate has liquefied and that fresh substrate can be added. If the power increases, this means that fresh substrate has just been added and more time must be allowed to regain the power before the addition.

In accordance with the invention, the measurement of said rheological characteristics of the reaction medium is monitored such that if a reduction in said value is detected over time, the following step a) is carried out:

a) the feeding flow rate of pre-treated lignocellulosic substrate is increased, with or without modification of the flow rate of enzymes and/or water;

and in that if an increase in said value is detected over time, a step b) is carried out as follows:

b) the feeding flow rate of water and/or enzymes is increased, with or without modification of the flow rate of pre-treated lignocellulosic substrate.

In the case in which said value is stable over time, the flow rates of substrate, enzyme and water are advantageously kept constant.

In accordance with a preferred embodiment, the process for the production of liquefied lignocellulosic substrate by enzymatic reaction in accordance with the invention advantageously operates in "fed batch" mode. In this case, said process is carried out in a continuously fed reactor, during which none of the contents of the reactor is withdrawn.

In accordance with another preferred embodiment, the process for the production of liquefied lignocellulosic substrate by enzymatic reaction in accordance with the invention advantageously operates in "chemostat" mode. In this case, said process is carried out in a continuously fed reactor during which a fraction of the reaction volume is withdrawn so as to keep the mass of the reaction volume constant.

In said preferred embodiment in which said process is carried out in a continuously fed reactor and in the case in which a reduction in said value is detected over time, said step a) is carried out in accordance with a first embodiment in which the feed flow rate for the pre-treated lignocellulosic substrate is increased, while the flow rate of enzyme and water are reduced so as to keep the reaction volume constant. In this case, the outlet flow rate remains constant.

Said step a) may advantageously also be carried out in accordance with a second embodiment in which the flow rate of pre-treated lignocellulosic substrate is increased along with the flow rates of enzyme and water so as to keep the concentration of enzyme and the dry matter content constant. The outlet flow rate is then increased to keep the reaction volume constant. In this case, the reaction time for liquefaction reduces.

Said step a) may also advantageously be carried out in accordance with a third embodiment in which the flow rate of pre-treated lignocellulosic substrate is increased while keeping the flow rates of enzyme and water constant. The outlet flow rate is then increased in order to keep the reaction volume constant. In this case, the reaction time for liquefaction reduces.

In said preferred embodiment in which said process is carried out in a continuously fed reactor and in the case in which an increase in said value is detected with time, said step b) is carried out in accordance with a first embodiment in which the flow rate of pre-treated lignocellulosic substrate is reduced while increasing the flow rate of enzyme and water so as to keep the reaction volume constant. The outlet flow rate remains constant.

Said step b) may also advantageously be carried out in accordance with a second embodiment in which the flow rate of pre-treated lignocellulosic substrate is reduced along with the flow rates of enzyme and water so as to keep the concentration of enzyme and the dry matter content constant. The outlet flow rate is then reduced in order to keep the reaction volume constant. In this case, the reaction time for liquefaction increases.

Said step b) may also advantageously be carried out in accordance with a third embodiment in which the flow rate of pre-treated lignocellulosic substrate is reduced while keeping the flow rates of enzyme and water constant. The outlet flow rate is also increased in order to keep the reaction volume constant. In this case, the reaction time for liquefaction increases.

Preferably, steps a) and b) are carried out by an operator or are automated using control software, for example.

The process of the present invention is advantageously operated at a temperature in the range 40° C. to 60° C., preferably in the range 45° C. to 55° C., at a pH in the range 4 to 6, preferably in the range 4.5 to 5, and at atmospheric pressure.

The agitation rate depends on the size of the reactor and the agitator.

In the case in which the value for the electrical power consumed by the motor is measured, said electrical power consumed by the motor with respect to the mass of the reaction volume advantageously remains in the range 0.05 to 4 kW/tonne, preferably in the range 0.5 to 2 kW/tonne.

The temperature is also a parameter which can be adjusted.

If the value of one of the rheological characteristics of the reaction medium which is measured over time is high and the ways of operating in step b) cannot reduce it, it is possible to increase the temperature for a period of less than 5 h, preferably less than 2 h. In this case, the temperature is increased so that it remains in the range 40° C. to 60° C., preferably in the range 45° C. to 55° C.

This increase in temperature temporarily accelerates the reaction, but has the result of deactivating the enzymes more rapidly. It is equivalent to a temporary increase in the enzyme concentration.

If the value of one of the rheological characteristics of the reaction medium which is measured over time is low and the ways of operating in step a) cannot increase it, it is possible to reduce the temperature for a period of less than 5 h, preferably less than 2 h. In this case, the temperature is reduced so that it stays in the range 40° C. to 60° C., preferably in the range 45° C. to 55° C.

The reaction slows down, but the enzymes are deactivated less quickly. This action is equivalent to a temporary drop in the enzyme concentration.

Thus, the process of the invention can be used to obtain a lignocellulosic substrate with a rheology which facilitates pumping as well as agitation thereof.

The liquefied lignocellulosic substrate obtained at the end of the process of the invention can thus be readily transferred to another reactor for any subsequent steps.

Thus, the process of the invention can advantageously be followed by any subsequent step allowing transformation of the liquefied lignocellulosic substrate obtained at the end of the process of the invention.

Thus, the process of the invention can advantageously be followed by a saccharification step. Said saccharification step can be used for the production of sugar by enzymatic hydrolysis and is carried out under conditions which are similar to the process of the invention, i.e. liquefaction but with a simpler agitation system and a lower agitation power.

In a preferred embodiment, the saccharification step is advantageously carried out in the presence of an alcoholigenic microorganism so as to obtain a fermentation must. In this case, the saccharification and the alcoholic fermentation are carried out in a single step using a process for simultaneous saccharification and fermentation known as the SSF process.

The process of the invention may also advantageously be followed by a step for the production of an acetone, butanol, ethanol (ABE) mixture, said step advantageously being carried out in the presence of the yeast *Clostridium aceobutylicum*.

The process of the invention may also advantageously be followed by a step for the production of chemical intermediates.

The operational example below is intended to illustrate the invention.

EXAMPLES

Example No 1, In Accordance with the Invention: Fed Batch Mode Liquefaction Process Example No 1 concerns a liquefaction process carried out in a fed batch mode. The principle consists of preparing a starter liquor with a portion of the pre-treated lignocellulosic substrate to be liquefied. This means that the reaction can be commenced with a pre-treated lignocellulosic substrate diluted to allow mixing. As the liquefaction progresses and the viscosity of the medium drops, fresh substrate can be added in order to make up the volume of the reactor and reach a high dry matter content.

The pre-treated lignocellulosic substrate under consideration was wheat straw. A suitable pre-treatment to render the straw reactive to hydrolysis is continuous steam explosion. Initially, a step for grinding and acid impregnation are required. A 10 to 20 mm screen is amply sufficient. The acid impregnation is carried out in a sulphuric acid solution with a dry matter content of 10%. The dose of acid was 0.50% by weight of sulphuric acid with respect to the dry matter. The biomass was drained and introduced into the steam explosion reactor.

Steam explosion was carried out under the following operating conditions:
T=200° C.
P=16 bar
residence time: 5 min
dry matter content in reactor: 20-25%

The pre-treated straw was then brought to a pH of 4.8 with a concentrated solution of potassium hydroxide, KOH, then could be compressed to obtain a dry matter content of 35%. The purity of the substrate as regards cellulose obtained after this type of pre-treatment was generally approximately 50% by weight.

The liquefaction step was carried out in a 4 $m^3$ reactor equipped with a Paravisc type agitator from EKATO. The enzymatic cocktail used was Cellic-CTec2 from Novozyme. The enzymatic solution had a protein concentration of 200 g/l and a density of approximately 1.2.

The operating conditions for the fed batch were as follows:
dry matter content of initial reaction medium: 10%
dry matter content of final reaction medium: 20%
enzyme concentration: 20 g of enzymatic solution/kg of cellulose
Paravisc agitation rate: 15 revolutions per minute
pH=4.8, adjusted using concentrated potassium hydroxide
temperature=50° C., regulated
additions of pre-treated lignocellulosic substrates: 5 additions each of 320 kg.

Initially empty, the reactor was filled with 1675 kg of water to which 686 kg of pre-treated lignocellulosic substrate was added. The reactor heating was started in order to reach the set level of 50° C. Once this level had been reached, all of the enzymes required were introduced, i.e. 40 kg of enzymatic solution. The reaction then commenced with a dry matter content of 10% and a reaction volume of approximately 2.4 $m^3$. We let the time of addition of the enzymes, corresponding to the start of the reaction, be t0. At t0, the electrical power consumed by the agitation motor with respect to the mass of the reaction medium was 4.0 kW/tonne. When the reaction was running, the electrical power consumed by the motor with respect to the mass of the reaction medium dropped and finished at 2.0 kW/tonne. A first addition of 320 kg of substrate was then added, making the electrical power consumed by the motor with respect to the mass of the reaction medium rise again. This procedure was repeated until 5 additions had been carried out. In general, the final addition was carried out at approximately t0+3 h. The reaction was allowed to continue for 3 h longer so as to drop the viscosity before being able to move to the subsequent step or to move into continuous mode. An electrical power consumed by the motor with respect to the mass of reaction medium of 0.5 kW/tonne at the end of liquefaction could be anticipated.

Example No 2, In Accordance with the Invention: Continuous Mode Liquefaction Process Starting from Fed Batch Example No 2 concerns a liquefaction process carried out in continuous mode starting from a fed batch mode as explained in Example No 1. The reagents and operating conditions of the "fed batch" mode remained the same. The transition from fed batch mode to continuous mode was made once the 4 m³ reactor was full and the electrical power consumed by the motor with respect to the mass of reaction medium was 1.0 kW/tonne. At that time, the product was withdrawn continuously at a flow rate that could maintain a constant reaction volume. For a residence time of 4 h, this corresponded to a flow rate of 1 tonne per hour. At that time, substrate, water and enzymes were injected at flow rates which were generally identical in order to keep the mass and volume in the reactor constant. The mass flow rate of each stream was thus as follows:
  water: 419 kg/h
  enzymatic solution: 10 kg/h
  substrate: 571 kg/h
Continuous liquefaction then commenced and three cases may arise:
  the electrical power consumed by the motor remains constant, in which case the flow rates of substrate, enzymatic solution or water are not modified
  the electrical power consumed by the motor reduces, in which case it is possible:
    to increase the substrate flow rate by reducing that of the enzyme and water in order to keep the volume constant. The outlet flow rate remains constant. Example: 650 kg/h of substrate, 9 kg/h of enzyme, 341 kg/h of water and an outlet flow rate of 1000 kg/h
    to increase the substrate flow rate by keeping the enzyme and water flow rates constant. The outlet flow rate also has to be increased in order to keep the volume constant. Example: 650 kg/h of substrate, 10 kg/h of enzyme, 419 kg/h of water and an outlet flow rate of 1079 kg/h.
  the electrical power consumed by the motor increases, in which case it is possible:
    to decrease the substrate flow rate by increasing that of the enzyme and water in order to keep the volume constant. The outlet flow rate remains constant. Example: 500 kg/h of substrate, 12 kg/h of enzyme, 488 kg/h of water and an outlet flow rate of 1000 kg/h
    to reduce the substrate flow rate by keeping the enzyme and water flow rates constant. The outlet flow rate also has to be adjusted to keep the volume constant. Example: 500 kg/h of substrate, 10 kg/h of enzyme, 419 kg/h of water and an outlet flow rate of 929 kg/h.

Depending on the changes in the electrical power consumed by the motor with respect to the mass of the reaction medium, it is thus possible to control the liquefaction process in this manner in order to maintain a duty point characterized by the viscosity at a given shear rate. The reasoning is similar with monitoring the agitation power or the torque.

Example 3, In Accordance with the Invention: Embodiments of Step a)

Example No 3 concerns the various embodiments of step a). The liquefaction reactor operated in a stable manner in continuous mode and the flow rates of substrate, water and enzyme were respectively 40 kg/h, 59 kg/h and 1 kg/h as indicated in the table, in the column "Nominal case".

A reduction in the rheological characteristic measured was detected over time.

Starting from the nominal case, the flow rate of substrate was increased from 40 to 50 kg/h, and the flow rates of water and enzyme were respectively reduced from 59 to 49.5 kg/h and from 1 to 0.5 kg/h. The total flow rate was conserved and the rheological characteristic which was measured was again at its nominal value. This embodiment is shown in the table, in the column "Case a)1)".

Starting from the nominal case, the flow rate of the substrate was increased from 40 to 50 kg/h, and the flow rates of water and enzyme were respectively increased from 59 to 73.75 kg/h and from 1 to 1.25 kg/h.

Compared with the nominal case, the ratio of the flow rate of water to the substrate flow rate and the ratio of the flow rate of enzyme to the substrate flow rate was conserved. The rheological characteristic measured was again at its nominal value. This embodiment is presented in the table in the column "Case a)2)".

Starting from the nominal case, in a third embodiment, the flow rate of substrate was increased from 40 to 50 kg/h, and the flow rates of water and enzyme were kept constant. The rheological characteristic measured was again at its nominal value. This embodiment is presented in the table in the column "Case a)3)".

TABLE 1

| | Embodiments of step a) - flow rates in kg/h | | | |
|---|---|---|---|---|
| Data | Nominal case | Case a)1) | Case a)2) | Case a)3) |
| Substrate flow rate | 40 | 50 | 50 | 50 |
| Water flow rate | 59 | 49.5 | 73.75 | 59 |
| Enzyme flow rate | 1 | 0.5 | 1.25 | 1 |
| Total flow rate | 100 | 100 | 125 | 110 |
| Effects | | Dose and DM content reduce | Dose and DM content constant | Dose and DM content reduce |

Example 4, In Accordance with the Invention: Embodiments of Step b)

Example No 4 concerns the various embodiments of step b). The liquefaction reactor operated in a stable manner in continuous mode and the flow rates of substrate, water and enzyme were respectively 40 kg/h, 59 kg/h and 1 kg/h as indicated in the table, in the column "Nominal case".

An increase in the rheological characteristic measured was detected over time.

Starting from the nominal case, in a first embodiment, the flow rate of substrate was decreased from 40 to 30 kg/h, and the flow rates of water and enzyme were respectively increased from 59 to 68.5 kg/h and from 1 to 1.5 kg/h. The total flow rate was conserved and the rheological characteristic which was measured was again at its nominal value. This embodiment is shown in the table, in the column "Case b)1)".

Starting from the nominal case, in a second embodiment, the flow rate of substrate was decreased from 40 to 30 kg/h, and the flow rates of water and enzyme were respectively reduced from 59 to 44.25 kg/h and from 1 to 0.75 kg/h.

Compared with the nominal case, the ratio of the flow rate of water to the flow rate of substrate and the ratio of the flow rate of enzyme to the substrate flow rate was conserved. The rheological characteristic which was measured was again at its nominal value. This embodiment is shown in the table, in the column "Case b)2)".

Starting from the nominal case, in a third embodiment, the flow rate of substrate was decreased from 40 to 30 kg/h, and the flow rates of water and enzyme were kept constant. The rheological characteristic which was measured was again at its nominal value. This embodiment is shown in the table, in the column "Case b)3)".

TABLE 2

Embodiments of step b) - flow rates in kg/h

| Data | Nominal case | Case b)1) | Case b)2) | Case b)3) |
|---|---|---|---|---|
| Substrate flow rate | 40 | 30 | 30 | 30 |
| Water flow rate | 59 | 68.5 | 44.25 | 59 |
| Enzyme flow rate | 1 | 1.5 | 0.75 | 1 |
| Total flow rate | 100 | 100 | 75 | 90 |
| Effects | | Dose and DM content increase | Dose and DM content constant | Dose and DM content increase |

The invention claimed is:

1. A process for the production of liquefied lignocellulosic substrate by enzymatic reaction and saccharification thereof, said process comprising:
   (i) conducting liquefaction of pre-treated lignocellulosic substrate by feeding pre-treated lignocellulosic substrate, water and one or more enzymes at desired flow rates into a reactor to form a reaction medium having a reaction volume, wherein the amount of said one or more enzymes is in the range of 0.1 to 60 mg per gram of cellulose and said pre-treated lignocellulosic substrate is at a concentration of 10% to 40% by weight dry matter,
   whereby said pretreated lignocellulosic substrate, is brought into contact, with said water and with said one or more enzymes, under agitation, for a time period in the range of 1 to 24 hours, to produce liquefied lignocellulosic substrate by enzymatic reaction,
   wherein dry matter concentration, expressed as percentage by weight, is the ratio of the mass of a sample of said pre-treated lignocellulosic substrate obtained after drying at 105° C. for 24 hours over the initial mass of said sample,
   wherein said pre-treated lignocellulosic substrate is introduced into said reactor in fed-batch mode or in continuous mode,
   wherein an electrical powered motor is used to provide said agitation, and
   wherein over time, at least the value of one of the rheological characteristics of the reaction medium is measured and in that if a reduction in said value is detected over time, a) is carried out:
   a) increasing the feeding flow rate of pretreated lignocellulosic substrate, with or without modification of the feeding flow rate of enzymes and/or water;
   and in that if an increase in said value is detected over time, b) is carried out as follows:
   b) increasing the feeding flow rate of water and/or said one or more enzymes, with or without modification of the feeding flow rate of pre-treated lignocellulosic substrate; and
   wherein the value that is measured is the electrical power consumed by said motor, and
   wherein the electrical power consumed by said motor with respect to the mass of the reaction volume remains in the range of 0.05 to 4 kW/ton; and
   (ii) subjecting liquefied lignocellulosic substrate from (i) to a saccharification step for production of sugar by enzymatic hydrolysis under agitation, wherein agitation is performed at lower power during saccharification than during said liquefaction of pre-treated lignocellulosic substrate, and saccharification is performed for longer than said liquefaction.

2. The process according to claim 1, wherein said pre-treated lignocellulosic substrate is brought into said contact with water and one or more enzymes at a concentration in the range 18% to 24% by weight of dry matter.

3. The process according to claim 1, wherein said one or more enzymes are brought into contact in an amount in the range 10 to 20 mg per gram of cellulose.

4. The process according to claim 1, wherein said time period is in the range of 4 to 8 hours.

5. The process according to claim 1, wherein said process is carried out in a continuously fed reactor and during said time period reaction volume is not withdrawn from the reactor.

6. The process according to claim 1, wherein said process is carried out in a continuously fed reactor and during said time period a fraction of the reaction volume is withdrawn so as to keep the mass of the reaction volume constant.

7. The process according to claim 1, wherein said saccharification step is carried out in the presence of an alcoholigenic microorganism in accordance with a simultaneous saccharification and fermentation process.

8. The process according to claim 1, wherein said process is operated at a temperature in the range of 40° C. to 60° C., at a pH in the range of 4 to 6, and at atmospheric pressure.

9. The process according to claim 1, wherein the electrical power consumed by said motor with respect to the mass of the reaction volume remains in the range of 0.5 to 2 kW/ton.

10. The process according to claim 1, wherein said pre-treated lignocellulosic substrate is brought into said contact with water and one or more enzymes at a concentration in the range 18% to 40% by weight of dry matter.

11. The process according to claim 1, wherein said pre-treated lignocellulosic substrate is brought into said contact with water and one or more enzymes at a concentration in the range 16% to 30% by weight of dry matter.

12. The process according to claim 1, wherein said pre-treated lignocellulosic substrate is brought into said contact with water and one or more enzymes at a concentration in the range 18% to 24% by weight of dry matter.

13. The process according to claim 1, wherein said one or more enzymes are brought into contact in an amount in the range of 5 to 30 mg per gram of cellulose.

14. The process according to claim 1, wherein said time period is in the range of 2 to 12 hours.

15. The process according to claim 1, wherein said process is performed at a temperature in the range of 45° C. to 55° C., at a pH in the range of 4.5 to 5, and at atmospheric pressure.

16. The process according to claim 1, wherein said pre-treated lignocellulosic substrate is obtained by acid impregnation and subsequent steam explosion.

17. The process according to claim 1, wherein in (i) the feeding of pre-treated lignocellulosic substrate is performed in fed-batch mode during which the pre-treated lignocellulosic substrate is fed into the reactor in batches and reaction volume is not withdrawn from the reactor.

18. The process according to claim 1, wherein in (i) the feeding of pre-treated lignocellulosic substrate is performed in continuous mode during which the pre-treated lignocellulosic substrate is fed continuously into the reactor while a fraction of the reaction volume is withdrawn so as to keep the mass of the reaction volume constant.

19. The process according to claim 1, wherein a) is carried out by increasing the feed flow rate of pre-treated lignocellulosic substrate, while the flow rate of enzyme and water are reduced so as to keep reaction volume constant, and outlet flow rate remains constant.

20. The process according to claim 1, wherein a) is carried out by increasing the flow rate of pre-treated lignocellulosic substrate and the flow rates of enzyme and water so as to keep the concentration of enzyme and the dry matter content constant, and the outlet flow rate is then increased to keep reaction volume constant.

21. The process according to claim 1, wherein a) is carried out by increasing the flow rate of pre-treated lignocellulosic substrate while the flow rates of enzyme and water remain constant, and outlet flow rate is increased in order to keep reaction volume constant.

22. The process according to claim 1, wherein b) is carried out by reducing the flow rate of pre-treated lignocellulosic substrate, increasing the flow rate of enzyme and water to keep reaction volume constant, and maintaining outlet flow rate constant.

23. The process according to claim 1, wherein after producing the liquefied lignocellulosic substrate in step (i) the liquefied lignocellulosic substrate is transferred to another reactor for performing said saccharification step (ii).

24. The process according to claim 1, wherein production of liquefied lignocellulosic substrate in (i) by liquefaction is initially performed under fed-batch mode, during which the pre-treated lignocellulosic substrate is fed into the reactor in batches and reaction volume is not withdrawn from the reactor, and then performed under continuous mode, during which the pre-treated lignocellulosic substrate is fed continuously into the reactor while a fraction of the reaction volume is withdrawn so as to keep the mass of the reaction volume constant.

* * * * *